US008691263B2

(12) United States Patent
Mirabella

(10) Patent No.: US 8,691,263 B2
(45) Date of Patent: Apr. 8, 2014

(54) EXTRACELLULAR MATRIX COMPRISING PLATELET CONCENTRATE AND CRYOPRECIPITATE POLYMERIZED IN SITU

(75) Inventor: Carlo Mirabella, Cortona (IT)

(73) Assignee: Azienda Ospedaliero-Universitaria Careggi, Florence (IT)

( * ) Notice: Subject to any disclaimer, the term of this patent is extended or adjusted under 35 U.S.C. 154(b) by 359 days.

(21) Appl. No.: 12/736,400

(22) PCT Filed: Apr. 3, 2009

(86) PCT No.: PCT/EP2009/054001
§ 371 (c)(1),
(2), (4) Date: Oct. 4, 2010

(87) PCT Pub. No.: WO2009/121953
PCT Pub. Date: Oct. 8, 2009

(65) Prior Publication Data
US 2011/0045051 A1    Feb. 24, 2011

(30) Foreign Application Priority Data

Apr. 4, 2008    (IT) ................ FI2008A0070

(51) Int. Cl.
*A61F 2/00* (2006.01)
(52) U.S. Cl.
USPC .............. 424/424; 424/423; 424/426
(58) Field of Classification Search
None
See application file for complete search history.

(56) References Cited

U.S. PATENT DOCUMENTS

| 2003/0095993 | A1 | 5/2003 | Bentz et al. ............ 424/426 |
| 2008/0206302 | A1* | 8/2008 | Sittinger et al. ............ 424/423 |

FOREIGN PATENT DOCUMENTS

| DE | 10 2005 030614 | 1/2007 | ............ A61F 2/08 |
| EP | 1 184 040 | 3/2002 | ............ A61L 27/38 |
| WO | WO 01/43787 | 6/2001 | ............ A61L 26/00 |
| WO | WO 02/43692 | 6/2002 | ............ A61K 9/00 |
| WO | WO 03/035115 | 5/2003 | |
| WO | WO 2008004260 A2 * | 1/2008 | |

OTHER PUBLICATIONS

Poruk "Serum Platelet Factor 4 Is an Independent Predictor of Survival and Venous Thromboembolism in Patients with Pancreatic Adenocarcinoma" Cancer Epidemiology, Biomarkers & Prevention, 2010, 19, 2605-2610.*
*International Search Report and Written Opinion for corresponding PCT Application No. PCT/EP2009/054001 dated Jan. 7, 2010.
*Yannas et al., *Wound Tissue can Utilize a Polymeric Template to Synthesize a Functional Extension of Skin*, American Assiciation for the Advancement of Science., vol. 215, Jan. 8, 1982 (pp. 174-176).
Formigli, et al., "Dermal matrix scaffold engineered with adult mesenchymal stem cells and platelet-rich plasma as a potential tool for tissue repair and regeneration," (2012) J. Tissue Eng. Regen. Med., vol. 6, pp. 125-134. doi: 10.1002/term.405 (first published online Feb. 24, 2011).

* cited by examiner

*Primary Examiner* — Jon P Weber
*Assistant Examiner* — Charles Zoltan Constantine
(74) *Attorney, Agent, or Firm* — Ohlandt Greeley Ruggiero & Perle, L.L.P.

(57) ABSTRACT

The present invention describes an extracellular matrix comprising human platelet derived growth factors, that permits the maximizing of therapeutic efficacy, combining the benefits of both components, to result in a more efficient and rapid integration of the matrix up to the structurally organized reconstruction of the neoformed tissue "in vivo".

7 Claims, 1 Drawing Sheet
(1 of 1 Drawing Sheet(s) Filed in Color)

Derma extracellular matrix integra®
comprising platelet factors

Application of a matrix of the invention
on an ulcer caused by venous insufficiency

EXTRACELLULAR MATRIX COMPRISING PLATELET CONCENTRATE AND CRYOPRECIPITATE POLYMERIZED IN SITU

FIELD OF THE INVENTION

The present invention relates to the field of tissue repair and/or regeneration.

STATE OF THE ART

The need to influence the processes of tissue repair to facilitate both the healing of wounds as well as the induction of the actual regeneration of damaged tissue following traumatic or pathological events (such as injuries, burning, surgical excision), has always been one of the major problems for those who deal with tissue reconstruction.

Tissue engineering originated as an attempt to construct tissue and organs outside the human body, based on the fact that almost all animal cells can be cultivated in the laboratory.

However, it should be remembered that cultured cells proliferate forming bidimensional layers only, which cannot be equipared to tissues, since these latter are three-dimensional structures having cells within or on their upper surface; therefore it is necessary to use artificial scaffolds in order to provide the cells with a suitable support (extracellular matrix) for tissue regeneration. It is obvious that it is extremely important to develop extracellular matrices able to provide an efficient means for the reconstruction of tissue that has been destroyed following traumatic or pathological events.

BRIEF DESCRIPTIONS OF THE FIGURES

The patent or application file contains at least one drawing executed in color. Copies of this patent or patent application publication with color drawings will be provided by the Office upon request and payment of the necessary fee.

SUMMARY

Figure 1:
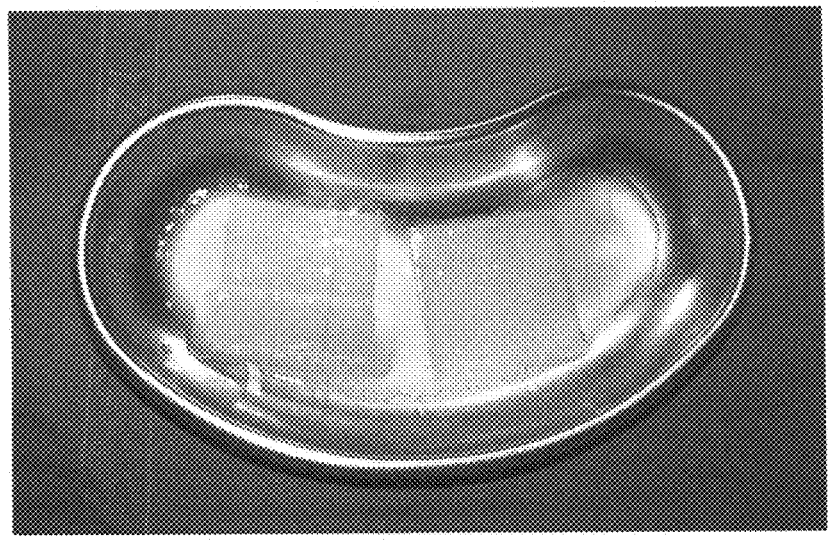
FIG. 1 shows a matrix according to the invention, immediately after preparation.

Described herein are extracellular matrices comprising platelet factors.

DETAILED DESCRIPTION OF THE INVENTION

The present invention allows to overcome the aforesaid drawbacks thanks to an extracellular matrix comprising human platelet derived growth factors that are able to maximise therapeutic efficacy by combining the benefits obtained from the two components, the matrix and the growth factors, reducing the inflammatory stage, thus anticipating cell migration and proliferation, resulting in a more efficient and rapid integration of the matrix until a structurally organised reconstruction of the neoformed tissue "in vivo" is achieved.

According to the invention, the term extracellular matrix refers to a bioengineered or heterologous matrix able to permit stable bonds between cells and the matrix (generally with the proteic and/or polysaccharidic component).

Therefore, the extracellular matrices according to the invention must have:

A porosity level that permits the cells to recreate a suitable micro-environment for the specific site and tissue type the capacity to communicate and exchange signals with the host cells, a suitable structure for vessel and cell growth, where necessary.

controlled degradation able to be metabolised and replaced by the extracellular matrix produced by the cells themselves.

Generally, the matrices assigned for dermal substitution according to the invention are composed of a double layer membrane, the part destined to replace the dermis having a porous structure.

In general, bio-engineered matrices are composed of any kind of tolerable and biocompatible biomaterial comprising a proteic and/or polysaccharidic component such as, for example, collagens, glycosaminoglycans (like hyaluronic acid), cellulose and/or combinations of these materials. In addition, biological human heterologous acellular matrices exist, such as de-epidermized dermis (DED) or which are derived from animals such as the matrix obtained from the submucosa of the small intestine of the pig.

It is preferable to provide three-dimensional matrixes with a porosity that permit the cells to recreate themselves in a suitable micro-environment for the specific site and tissue type.

In particular, it is preferable to provide matrices with porosity able to permit the adsorption of the platelets and the proteins contained in the cryoprecipitate in order to achieve a therapeutic platelet concentration of approximately $1\text{-}2\times10^9$ per mL.

Given the aforesaid conditions, generally it is estimated that the useful matrices according to the invention should have pores with a diameter over 2 microns.

The membrane forming the dermal matrix can be coated (or not) with a film in a semi-permeable material such as polysiloxane or an elastomer, which forms the part that replaces the epidermis.

Matrices without film are normally used to add thickness to the dermis regeneration layer, during the treatment of deep wounds.

The dermal portion acts as a scaffolding for the infiltration of fibroblasts, macrophagy, lymphocyte, and capillary endothelial cells that form the neo-vascular network. As health improves, the matrix layer is reabsorbed and a new extracellular matrix is deposited by the fibroblasts to form the neodermis. Where the vascularization of the neodermis is adequate, and on condition that autografting is available, any film that was used to replace the epidermis can be removed, and if necessary, a fine layer of epidermal autograft is positioned on the neodermis. The epidermal graft cells grow and form a mature epidermis providing a functional dermis and epidermis.

A particular example of an extracellular matrix according to the invention is the Integra® matrix (Integra Lifesciences Corp., Plainsboro, N.J., USA).

The term platelet factors refers to the therapeutic components of blood that can be obtained through liberating alpha granules obtained during the aggregation of a platelet concentrate placed in contact with calcium and biological or pharmalogical proaggregant factors (thrombin).

Said platelet factors can obviously be either autologous or heterologous or recombinant.

In particular, according to the invention, as well as other biochemical mediators that are released by the platelets themselves, the platelet factors find themselves in a preparation composed of fibrin glue, platelet gel, thrombin or a mixture thereof.

All these components are involved in the tissue repair/regeneration and can be of either autologous or heterologous origin.

To prepare the extracellular matrices according to the invention, the platelet gel and the fibrin glue are formed "in situ" inside the matrix through the action, respectively, of the thrombin on the platelet concentrate (PRP) and on the cryoprecipitate (CRIO) previously used to impregnate the matrix.

In particular, after having prepared the matrix according to the user instructions printed in the manufacturer's illustrated catalogue, it is rinsed with physiological solution eliminating all excess and is deposited in a flat-based container, such as a surgical tray.

A syringe is used to place drops of the PRP/CRIO on the matrix in a large enough quantity to ensure that the matrix is completely imbibed (normally in a ratio of 2:1 in volume), then it is shaken gently, and left to settle, the procedure being repeated several times. Then, using a syringe, drops of a mixture of calcium gluconate and thrombin are placed on the matrix, shaken gently, and then left to settle until the gel is formed.

The matrix prepared in this manner can be used immediately, or can be maintained at a lower temperature at −25° C. and defrosted just before use. Preferably, the calcium gluconate is in a 10% aqueous solution and the calcium gluconate/thrombin ratio is 1:5 to 1:10 in volume.

The ratio (mixture of calcium gluconate and thrombin)/(PRP-CRIO) is preferably 1:10, but it can be reduced, to 1:5 for example, on condition that the platelet and/or fibrinogenic concentration is not reduced under the therapeutic concentration level.

The thrombin can be obtained using conventional known methods, such as by plasma or cryoprecipitate recalcification.

This procedure is performed under a sterile safety hood by taking the plasma or the cryoprecipitate from the bag using a syringe, and adding 10% calcium gluconate in a ratio of 1:5 to 1:10 in volume.

Following the recalcification process, after about 20 minutes, the product is subjected to high speed centrifuge (3000 rpm) for 15 minutes to obtain the buffy-coat serum rich in thrombin.

The platelet concentrate used for the invention can be obtained using conventional known methods from:
- platelets from homologous single unit/single buffy-coat, setting up a pool, it is connected to a transfer bag using a sterile connector, centrifuged at 3500 rpm for 15 minutes. The platelet pellet thus obtained is resuspended in approximately 50-60 mL of plasma;
- platelets from homologous multicomponent apheresis, the platelet apherisis is directly centrifuged to proceed as described above;
- autologous whole blood, a unit of platelets is obtained from a single buffy-coat in a quadruple bag and, it is connected to a transfer bag using a sterile connector, centrifuged at 3500 rpm for 15 minutes, after which the buffy-coat which is eliminated is used to produce the autologous thrombin. The platelet pellet thus obtained is resuspended in approximately 10-15 mL of plasma;
- autologous multicomponent apheresis using a cellular separator and a dedicated procedure is performed to obtain a platelet apherisis of approximately 20 mL (wherein the volume can be modified according to the needs of the patient without affecting the final platelet concentration) with a yield of $3.5 \times 10^6$ platelets per microlitre, a unit of plasma of 200 mL, and a unit of buffy-coat of approximately 30 mL with a white globule concentration (containing monocytes and stem cells) of approximately $50\text{-}60 \times 10^3$ per microlitre and a platelet concentration of approximately $1.5 \times 10^9$ per mL. The platelet apherisis is used without any further manipulation. The plasma is frozen to produce cryoprecipitate;
- Miniaturised systems, generally closed circuit, which are commercially available and dedicated for the production of autologous platelet gel taken from a blood sample of 8 to approximately 150 mL. A specific technical-operating protocol for each of these systems is provided by the manufacturer together with the instrument pack.

The CRIO used in the invention is a preparation composed of the cryoglobulinic fraction of fresh plasma, obtained from a single donation, concentrated to a final volume no greater than 40 mL.

As well as the VIII factor, the product also contains the major part of the Von Willebrand factor, fibrinogen, XIII factor and fibronectin, present in the initial fresh plasma.

The CRIO can be obtained in a known manner from fresh frozen plasma from apheresis or separation plasma after having connected a transfer bag using a sterile connector and thawed to 4° C.±2° C. overnight, decantation is performed by resuspending the cryoprecipitate in approximately 40 mL of waste plasma (obtained from fresh frozen plasma without cryoprecipitate), the fibrinogen content must not be less than 3.5 mg/ml.

Therefore, as can be understood from the descriptions above, the platelet concentrate, the cryoprecipitate and the thrombin are prepared using simple physical methods.

To assemble the PRP and CRIO, closed circuit can be used with sterile connections to mix the PRP and the CRIO in a ratio of 1:1 to obtain a hemocomponent having the properties of both components.

The topical use of the matrix prepared in this manner is facilitated because of its plasticity and conformable characteristics in the application site, facilitating and accelerating the tissue repair.

Obviously, as well as dermis regeneration, as specifically described above and illustrated in the following examples, the matrices according to the invention can also be applied to the regeneration of other types of tissue such as tendons, cartilage, muscle and bone.

EXAMPLE 1

Preparation of the Dermal Matrix Integra® "Dermal Regeneration Template" Enriched With PRP/CRIO Throughout the entire matrix preparation, PRP/CRIO and thrombin must be handled using aseptic techniques, and the manufacturer's instructions for product preparation must be followed with care.

A matrix Integra® "dermal regeneration template" is used, and after washing with a physiological solution it is blotted several times with sterile gauze to absorb any excess physiological solution.

The matrix is placed on a flat-based sterile container, such as a surgical tray for example, with the silicon part on the underside.

Using a syringe, drops of PRP/CRIO are placed on the matrix in a ratio of 2:1 in volume (matrix Integra® surface 5×5 mm, thickness approximately 1.5 mm, volume approximately 3.75 ml; PRP/CRIO necessary approximately 7.5 ml)

The container is shaken gently 5-6 times and left to settle for 10 minutes, after which the procedure is repeated.

Using a syringe, drops of a mixture of calcium gluconate 10% and thrombin (1:5) are added in a ratio of 1:10 with PRP/CRIO used to enrich the matrix and the container is shaken gently 5-6 times.

It is left to settle for 5-10 minutes until the gel is formed. Gelification is controlled by tipping the container on a 45° angle.

The matrix is ready for application, which can be immediately performed.

EXAMPLE 2

Method for the Preparation of the Dermal Matrix Integra® "Dermal Regeneration Template Single Layer" Enriched With PRP/CRIO Throughout the entire matrix preparation, PRP/CRIO and thrombin must be handled using aseptic techniques, and the manufacturer's instructions for product preparation must be followed with care.

A matrix Integra® "dermal regeneration template single layer" is used, and after washing with a physiological solution, it is blotted several times with a sterile gauze to absorb any excess.

The matrix is placed on a flat-based sterile container, such as a surgical tray for example, in contact with the bottom of the tray.

Using a syringe, drops of PRP/CRIO are placed on the matrix in a ratio of 2:1 in volume (matrix Integra® surface 5×5 mm, thickness approximately 1.5 mm, volume approximately 3.75 ml; PRP/CRIO necessary approximately 7.5 ml) The container is shaken gently 5-6 times and left to settle for 10 minutes.

The dermal matrix is overturned inside the container and this is shaken gently 5-6 times, then left to settle for 10 minutes.

Using a syringe, drops of a mixture of calcium gluconate 10% and thrombin (1:5) are added in a ratio of 1:10 with PRP/CRIO used to enrich the matrix and the container is shaken gently 5-6 times.

It is left to settle for 5-10 minutes until the gel is formed. Gelification is controlled by tipping the container on a 45° angle.

The matrix is ready for application, which can be performed immediately.

Figure 2:
FIG. 2 shows an example of an application of a matrix according to the invention

FIG. 1 shows a matrix according to the invention immediately after its preparation, while FIG. 2 shows the rapid reconstruction of the neodermis followed by wound care and healing by second intention, following the application of a matrix according to the invention on an ulcer caused by venous insufficiency.

What is claimed is:

1. A three-dimensional extracellular matrix composed of a single or double layer membrane wherein the part of the matrix destined to replace the dermis is a porous structure comprising platelet factors, wherein said platelet factors are in a preparation composed of
    fibrin glue and platelet gel formed in situ inside said porous structure of the matrix through the action of thrombin on a platelet concentrate and on a cryoprecipitate comprising fibrinogen previously used to impregnate said porous structure of the matrix.

2. The matrix according to claim 1 wherein said matrix is bioengineered or heterologous.

3. The matrix according to claim 2 wherein said bioengineered matrix is composed of any type of tolerable and biocompatible biomaterial comprising a proteic and/or polysaccharidic component.

4. The matrix according to claim 2 wherein said heterologous matrix is a matrix of biological human and/or animal origin.

5. The matrix according to claim 2, wherein said extracellular bioengineered and/or heterologous matrices are able to permit stable bonds between cells and matrix.

6. The matrix according to claim 1 wherein said matrix is coated with a semi permeable material film that forms the part which replaces the epidermis.

7. The matrix according to claim 1, further comprising monocytes and/or stem cells.

* * * * *